United States Patent
Pyhälahti et al.

(10) Patent No.: US 11,964,936 B2
(45) Date of Patent: Apr. 23, 2024

(54) PROCESS FOR MANUFACTURING OLEFIN TRIMERS AND TETRAMERS

(71) Applicant: Neste Oyj, Espoo (FI)

(72) Inventors: Antti Pyhälahti, Porvoo (FI); Jaana Kanervo, Porvoo (FI)

(73) Assignee: NESTE OYJ, Espoo (FI)

(*) Notice: Subject to any disclaimer, the term of this patent is extended or adjusted under 35 U.S.C. 154(b) by 0 days.

(21) Appl. No.: 18/252,922

(22) PCT Filed: Oct. 27, 2022

(86) PCT No.: PCT/FI2022/050703
§ 371 (c)(1),
(2) Date: May 15, 2023

(87) PCT Pub. No.: WO2023/073284
PCT Pub. Date: May 4, 2023

(65) Prior Publication Data
US 2023/0391688 A1    Dec. 7, 2023

(30) Foreign Application Priority Data
Oct. 27, 2021 (FI) .................................. 20216108

(51) Int. Cl.
*C07C 5/03* (2006.01)

(52) U.S. Cl.
CPC ...................... *C07C 5/03* (2013.01)

(58) Field of Classification Search
CPC .. C07C 5/03; C07C 5/25; C07C 11/02; C07C 2/08; C07C 2/02; C07C 2/06; C07C 2/04; C07C 7/04
See application file for complete search history.

(56) References Cited

U.S. PATENT DOCUMENTS

| | | | |
|---|---|---|---|
| 2,572,724 A | 10/1951 | Hinds et al. | |
| 10,793,488 B2* | 10/2020 | Stochniol | ................ C07C 7/04 |
| 2020/0123080 A1 | 4/2020 | Stochniol et al. | |
| 2020/0361835 A1 | 11/2020 | Stochniol et al. | |
| 2022/0289644 A1* | 9/2022 | Lotz | .................. C10M 177/00 |

FOREIGN PATENT DOCUMENTS

| | | |
|---|---|---|
| EP | 2949636 A1 | 12/2015 |
| WO | 2012076758 A2 | 6/2012 |
| WO | 2020081212 A1 | 4/2020 |
| WO | 2021029938 A1 | 2/2021 |
| WO | 2021029939 A1 | 2/2021 |

OTHER PUBLICATIONS

International Search Report (PCT/ISA/210) and Written Opinion (PCT/ISA/237) dated Jan. 31, 2023, by the European Patent Office as the International Searching Authority for International Application No. PCT/FI2022/050703. (13 pages).
Search Report dated Feb. 2, 2022, issued by the Finnish Patent and Registration Office in corresponding Finnish Application No. 20216108 (2 pages).

* cited by examiner

*Primary Examiner* — Sharon Pregler
(74) *Attorney, Agent, or Firm* — BUCHANAN INGERSOLL & ROONEY PC (57) ABSTRACT

A process for controlled manufacturing of olefin trimers and olefin tetramers is disclosed, wherein the olefin monomers are processed into olefin trimers and olefin tetramers by a two-step catalytic process involving separation and recycling of reaction products.

22 Claims, 1 Drawing Sheet

PROCESS FOR MANUFACTURING OLEFIN TRIMERS AND TETRAMERS

TECHNICAL FIELD

The present disclosure generally relates to a process for manufacturing olefin trimers and tetramers. The disclosure relates particularly, though not exclusively, to a continuous process which can be controlled such that the production of olefin trimers and olefin tetramers can be adjusted as desired.

BACKGROUND

This section illustrates useful background information without admission of any technique described herein representative of the state of the art.

Olefins are hydrocarbons containing at least one double bond. Olefins can be used as a valuable feedstock in fuels and fuel blends. Depending on the source, olefins can vary in size, degree of branching, and also the position and number of the double bond(s).

Smaller olefin molecules may be upgraded to produce longer chain molecules, i.e. oligomers of olefin monomers. Oligomerization reactions involve contacting olefin monomers with a catalyst to produce a longer chain molecule composed of olefin monomers.

SUMMARY

The appended claims define the scope of protection. Any example, description or drawing of an apparatus, product, or method which is not covered by the claims is presented herein not as an embodiment of the invention, but as background art or as an example which may be useful for understanding the invention.

According to a first aspect there is provided a process for controlled manufacturing of olefin trimers and olefin tetramers comprising:
  a. feeding at least one olefin monomer and at least one oxygen-containing moderator into at least one first reactor unit containing a catalyst;
  b. operating at least one of the first reactor unit(s) at a temperature selected from the range 30-140° C. and at a pressure selected from the range 800-5000 kPa for carrying out catalytic reactions between olefins inside the first reactor unit;
  c. withdrawing a first reactor outlet stream from at least one of the first reactor unit(s);
  d. distilling the first reactor outlet stream in a first distillation column to separate at least a first distillate comprising at least unreacted olefin monomers, and a first bottom product comprising at least dimers of the olefin monomers;
  e. feeding the first bottom product into at least one second reactor unit containing a catalyst;
  f. operating at least one of the second reactor unit(s) at a temperature selected from the range 30-140° C. and at a pressure selected from the range 150-5000 kPa for carrying out catalytic reactions between olefins inside the second reactor unit;
  g. withdrawing a second reactor outlet stream from at least one of the second reactor unit(s); and
  h. distilling the second reactor outlet stream in a second distillation column to separate a second distillate comprising at least olefin dimers, and a second bottom product comprising at least trimers and/or tetramers of the olefin monomers; and wherein the process further comprises controlling the composition of the second reactor outlet stream by:
  i. feeding olefin dimers into at least one of the first reactor unit(s) to increase the amount of olefin trimers in the second reactor outlet stream; and/or
  ii. feeding olefin dimers into at least one of the second reactor unit(s) to increase the amount of olefin tetramers in the second reactor outlet stream.

In an embodiment in the steps i. and ii. the expression "feeding olefin dimers" comprises or consists of feeding of olefin dimers of the second distillate. Additionally or alternatively, olefin dimers can be fed from another source in any or both of these steps.

An advantage of the present process is high carbon efficiency. The process converts olefin monomers efficiently and with high yield into olefin trimers and/or olefin tetramers.

In an embodiment at least a portion of the olefin dimers formed during the process are recycled to at least one of the first reactor unit(s) and/or to at least one of the second reactor unit(s), and wherein a recycling ratio of the olefin dimers between the first reactor unit and the second reactor unit is selected from the range 0-100%.

Figure 1:
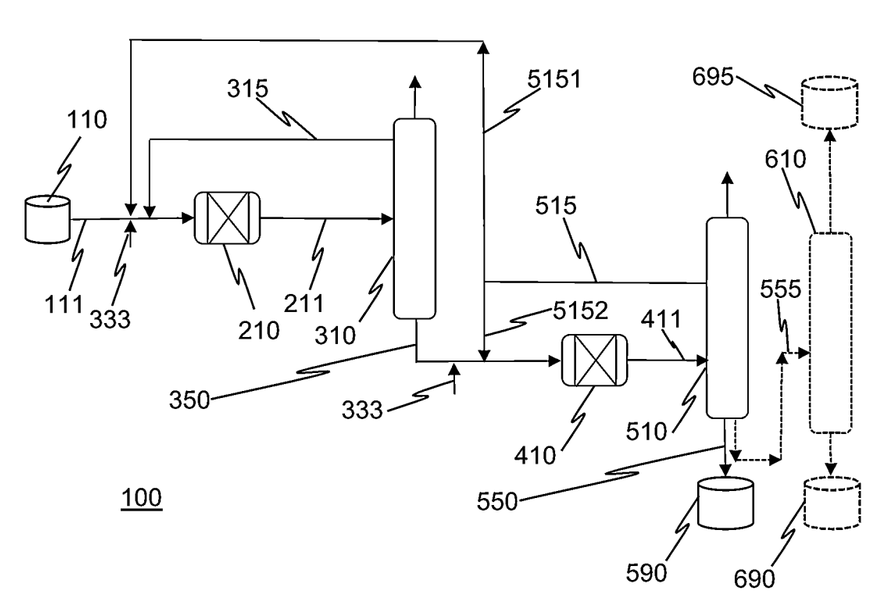

When olefin dimers are recycled into the first reactor unit(s), the dimers are preferably fed into the first reactor unit(s) through a reactor feed line, such as the first reactor feed line 11 shown in FIG. 1. Efficient mixing of recycled dimers with the fresh olefin monomers is thereby achieved.

In an embodiment, when olefin trimers are produced, the amount of recycled dimer compared to the fresh monomer in at least one of the first reactor unit(s) is at least about 350%, preferably at least about 400%, or about 350-550%, preferably about 400-500%, or about 450%. Preferably no dimer is recycled to the second reactor unit(s) when only olefin trimer production is desired. In another embodiment the operating conditions are as specified in Table 1. The amount of the recycled dimer compared to the fresh monomer may refer to the amount in one first reactor unit, or in two, in three, in four, or in all first reactor units comprising the first reaction zone.

In an embodiment, when olefin tetramers are produced, the total amount of recycled components compared to the fresh monomer is at least about 250%, preferably at least about 300%, or about 250-350%, preferably about 300-350%, or about 320%. Preferably dimer is recycled to at least one of the second reactor unit(s) when olefin tetramers are produced, and the amount of recycled dimer compared to the fresh monomer is at least about 100%, such as 100-200% or 100-150% or about 140%. In another embodiment the operating conditions are as specified in Table 1. The amount of the recycled dimer compared to the fresh monomer may refer to the amount in one reactor unit, or in two, in three, in four, or in all reactor units comprising a reaction zone.

In an embodiment the operating temperature of at least one of the first reactor unit(s) and/or at least one of the second reactor unit(s) is selected from the range 50-140° C., or from the range 40-120° C., or from the range 45-120° C., or from the range 50-120° C. Another temperature range which can be used in the at least one first reactor unit(s) and/or at least one second reactor unit(s) is a temperature selected from the range 45-110° C., or from the range 50-110° C. In another embodiment said temperature is selected from the range 60-110° C.

In another embodiment in the first reactor unit the temperature is selected from the range 90-110° C., or from the range 95-105° C., such as about 100° C. When olefin trimers are produced, the temperature in the second reactor unit can be selected from the range 30-50° C., such as about 40° C. When olefin tetramers are produced, the temperature in the second reactor unit can be selected from the range 90-110° C., or from 95-105° C., such as about 100° C.

In an embodiment the operating weight hour space velocity of at least one of the first reactor unit(s) is selected from the range 1-10 1/h, and/or the operating weight hour space velocity of at least one of the second reactor unit(s) is selected from the range 0.05-100 1/h.

In an embodiment, when olefin trimers are produced, the operating weight hour space velocity of at least one of the first reactor unit(s) is selected from the range 1-1/h, or from the range 1-2 1/h. In another embodiment the operating weight hour space velocity of at least one of the second reactor unit(s) is selected from the range 1/h, or from 0.1-0.2 1/h, such as about 0.15 1/h. In another embodiment the WHSV is as specified in Table 1.

In an embodiment, when olefin tetramers are produced, the operating weight hour space velocity of at least one of the first reactor unit(s) is selected from the range 1-5 1/h, or from the range 1-2 1/h. In another embodiment the operating weight hour space velocity of at least one of the second reactor unit(s) is selected from the range 0.2-0.5 1/h, or from 0.3-0.4 1/h, such as about 0.35 1/h. In another embodiment the WHSV is as specified in Table 1.

In an embodiment the operating pressure of at least one of the first reactor unit(s) is selected from the range 2400-3000 kPa.

In an embodiment the operating pressure of at least one of the second reactor unit(s) is selected from the range 1900-2300 kPa. In another embodiment the operating pressure of at least one of the second reactor unit(s) is selected from the range 150-2300 kPa, such as from the range 300-2300 kPa or 400-2300 kPa.

In an embodiment the pressure in the first reactor unit is higher than the pressure in the second reactor unit.

In an embodiment the operating pressure of at least one of the first reactor unit(s) is selected from the range 2500-2700 kPa such as about 2600 kPa, and/or the operating pressure of at least one of the second reactor unit(s) is selected from the range 2000-2200 kPa such as about 2100 kPa. In an embodiment the pressure in at least one of the first reactor unit(s) is higher than the pressure in at least one of the second reactor unit(s).

In an embodiment the amount of the oxygen-containing moderator in at least one of the first reactor unit(s) is selected from the range 1000-15000 mol-ppm and/or the amount of the oxygen-containing moderator in at least one of the second reactor unit(s) is selected from the range 10-10000 mol-ppm or 10-2500 mol-ppm.

In an embodiment the amount of the oxygen-containing moderator in at least one of the first reactor unit(s) is selected from the range 2000-15000 mol-ppm, or from 2200-2800 mol-ppm, such as about 2600 mol-ppm.

In an embodiment the amount of the oxygen-containing moderator in at least one of the second reactor unit(s) is selected from the range 5-20 mol-ppm, or from the range 5-15 mol-ppm, such as about 10 mol-ppm. This amount is advantageous when producing olefin trimers. In another embodiment the amount of oxygen-containing moderator (oxygenate) is as specified in Table 1.

In an embodiment the amount of the oxygen-containing moderator in at least one of the second reactor unit(s) is selected from the range 500-2500 mol-ppm, or from the range 1000-2000 mol-ppm, such as about 1500 mol-ppm. This amount is advantageous when producing olefin tetramers. In another embodiment the amount of oxygen-containing moderator (oxygenate) is as specified in Table 1.

The choice of oxygenate concentration guide reaction selectivities in the present process: in the first reactor unit(s) the selectivity is balanced between dimer and trimer oligomers: the more oxygenate is supplied the more dimers over trimers are formed, in the second reactor unit(s) the more oxygenate is supplied the more tetramerization is suppressed thus preserving entering trimers composition. The extremes of the bottom product of the first column are a dimer dominated product with traces of heavier oligomers, or a trimer dominated product with traces of heavier oligomers.

Olefin monomers and possible solvent reside in all operation modes in the first reactor unit(s) and the first column, and they do not enter the second reactor unit(s).

In the present process the selectivity of the end products is controlled by the oxygenate concentration that determines product selectivity within each reactor unit, the operation mode of the first column, and the recycling ratio of the dimers from the second column in between the first and the second reactor unit(s).

In the trimer dominated operation mode dimers reside in the first reactor unit(s) and in the first column, and they do not enter the second reactor unit(s).

In an embodiment olefin trimers are not recycled from the second distillate to the first reactor or to the second reactor.

In the mixed degree operation mode all the targeted trimers are produced in the first reactor unit(s) and the first column regime, whereas the dimers withdrawn from the first column bottom are converted into tetramers in the second reactor unit(s).

In the maximal tetramer product dominated operation mode dimer production is favored in the first reactor unit(s) by controlling the amount of oxygenate. Optionally the monomer once-through conversion is kept below 90%. Optionally monomers from the first column top are recycled to the first reactor unit(s) and by withdrawing dimer with minimal higher oligomers from first column bottom. Therefore, in the second reactor unit/reaction zone dimers dimerize into tetramers in a controlled manner and all the unreacted dimers are recycled to the second reactor unit/reaction zone.

In an embodiment the amount of solvent feed is 0-80 weight-%, preferably 0-60 weight-%, based on the target of end product composition and subsequent operation mode of the first reactor unit/reaction zone. In cases where a substantial trimer proportion in the product is targeted, the solvent can be completely omitted. In the tetramer dominated operation mode a definite solvent fraction may be needed to control the exothermic nature of reactions in the first reactor unit/reaction zone. The degree of dimerization targeted for the first reactor unit(s) determines the need for solvent (all dimer 50-80% solvent, all trimer 0% solvent). In all cases where solvent is used it is recycled from the first column to the first reactor unit/reaction zone and solvent does not enter the second reactor unit/reaction zone.

In an embodiment where tetramer is the dominating product and feed does not contain a suitable inert solvent component, an additional solvent feed may be necessary. When added solvent is used, a main part of the solvent is recycled via the first reactor unit/reaction zone and the first column, and only a minor make-up feed is necessary. Further, an industrial feed may contain sufficient amount of suitable solvent as an impurity, and in such case no additional solvent feed is necessary.

Moreover, an industrial feed may contain light inert impurities such as paraffinic hydrocarbons with the same carbon number as the reactive olefin(s), which may accumulate to the recycle streams. In such case a purge stream may be taken from the top of the column. If flow rate of the purge stream is substantial it may be advantageous to take the recycle stream as a side stream below the top of the column in order to prevent loss of the dimers present in the recycle stream.

In an embodiment the olefin monomers comprise olefins having four carbon atoms, preferably isobutene. In another embodiment the isobutene comprises 10-100 weight-% of the fresh olefin feed fed into the first reactor unit.

In an embodiment the olefin monomers are fed into at least one of the first reactor unit(s) in an olefin feed comprising at least one of the following: C4 olefins, C5 olefins, a mixed feed of C4 and C5 olefins, isobutene, 1-butene, cis-2-butene, trans-2-butene or any mixture thereof; and optionally comprising inerts, n-butane, i-butane, butadiene, distillation fraction, or any mixture thereof.

In an embodiment at least one of the catalyst(s), or the catalyst, is an acid catalyst, preferably a strongly acidic ion exchange resin catalyst, most preferably macroreticular acid ion exchange resin catalyst. The catalyst used in the first reactor unit or reaction zone may be the same catalyst as used in the second reactor unit or reaction zone. It is also possible to use a different catalyst in the first reactor unit (or reaction zone) and in the second reactor unit (or reaction zone).

In an embodiment the oxygen-containing moderator comprises water, demiwater, alcohol, tert-butyl alcohol, or any combination thereof.

In an embodiment the process further comprises increasing the amount of olefin trimers in the final product stream, or in the second reactor outlet stream, by recycling olefin dimers present in the second distillate to at least one of the first reactor unit(s).

In an embodiment 0-50 weight-% of the olefin dimers present in the second distillate are recycled to at least one of the first reactor unit(s) to obtain a ratio of trimers to tetramers of 25-0.05 (wt/wt) in the second reactor outlet stream.

In an embodiment 0-50 weight-% of the second distillate is recycled to at least one of the first reactor unit(s) to obtain a ratio of trimers to tetramers of 25-0.05 (wt/wt) in the second reactor outlet stream. As the second distillate contains dimers, the process can be directed to favor production of olefin trimers by increasing the amount of olefin dimers in the first reaction unit. When production of trimers is desired, the amount of second distillate recycled to the first reactor unit can be increased, for example 5-50, 10-50, 20-50, 30-50, or 40-50 wt-% of the second distillate can be recycled to the first reactor unit.

In an embodiment the process further comprises distilling the second bottom product in a third distillation column to separate a third distillate comprising trimers of the olefin monomers, and a third bottom product comprising tetramers of the olefin monomers.

In an embodiment the process further comprises increasing the amount of olefin tetramers in the second reactor outlet stream by recycling olefin monomers of the first distillate to at least one of the first reactor unit(s) in order to increase the production of olefin dimers in the first reactor unit, by feeding the first bottom product to at least one of the second reactor unit(s), and by recycling olefin dimers of the second distillate to at least one of the second reactor unit(s). By recycling olefin monomers to the first reactor unit the production of olefin dimers is enhanced, and these olefin dimers are reacted after distillation in the second reactor unit. To the second reactor unit dimers are also recycled from the second distillation column, and thereby the amount of olefin dimers in the second reactor is increased, which favors formation of olefin tetramers in the second reactor unit.

In an embodiment 99-100 weight-% of the olefin monomers present in the first distillate are recycled into at least one of the first reactor unit(s) and the first bottom product contains 2-98 weight-% of olefin dimers.

In an embodiment dimers are recycled only to at least one of the second reactor unit(s).

In an embodiment 4-99% or 4-96% of olefin monomers are converted to olefin trimers in the process.

In an embodiment 4-99% or 4-94% of olefin monomers are converted to olefin tetramers in the process.

The present process allows a high carbon efficiency with respect to the reactive olefin monomer: in high purity olefin feed case >99% of monomers end up in the product oligomers, whereas minor losses can be expected in the mixed feed cases where purge stream from the top of the first column might carry some reactive monomer over (<1-5%).

According to a second aspect is provided an olefin conversion system configured to carry out the process of the first aspect and comprising:

a. at least one first reactor unit configured to receive an acid catalyst;
b. at least one second reactor unit configured to receive an acid catalyst;
c. a first distillation column configured to separate olefin monomers from olefin dimers;
d. a second distillation column configured to separate olefin dimers from olefin trimers and olefin tetramers;
e. at least one first reactor feed line in fluid connection with at least one of the first reactor unit(s), and at least one reservoir for olefin monomers;
f. a first reactor outlet stream line in fluid connection with at least one of the first reactor unit(s) and the first distillation column;
g. a first recycle line in fluid connection with at least one of the first reactor unit(s) and the first distillation column;
h. a first bottom product line in fluid connection with the first distillation column and at least one of the second reactor unit(s);
i. a second reactor outlet stream line in fluid connection with at least one of the second reactor unit(s) and the second distillation column;
j. a second recycle line in fluid connection with the second distillation column, at least one of the first reactor unit(s), and at least one of the second reactor unit(s);
k. a second bottom product line in fluid connection with the second distillation column and a reservoir for the end product; and
l. an optional third distillation column configured to separate olefin trimers from olefin tetramers and comprising a third column feed line in fluid connection with the second bottom product line; and
m. an optional solvent make-up line connected to the first reactor feed line.

In an embodiment the present olefin conversion system comprising the above elements is configured to carry out the process of the first aspect or any of its embodiments or features.

In an embodiment the present olefin conversion system comprises means configured to control the flow in the second recycle line such that the recycled olefin dimers can be directed to at least one of the first reactor unit(s) and to at least one of the second reactor unit(s) at desired amounts and proportions.

According to another aspect is provided a method of operating the present olefin conversion system, comprising controlling the composition of the second reactor outlet stream by feeding olefin dimers into at least one of the first reactor unit(s) to increase the amount of olefin trimers in the second reactor outlet stream; and/or by feeding olefin dimers into at least one of the second reactor unit(s) to increase the amount of olefin tetramers in the second reactor outlet stream.

BRIEF DESCRIPTION OF THE FIGURES

FIG. 1 schematically shows the process for manufacturing olefin trimers and olefin tetramers. In an embodiment the present process is carried out according to the scheme of FIG. 1. The present olefin conversion system can also be used to carry out the process described in FIG. 1. The optional operating mode using a third column to separate olefin trimers from olefin tetramers is shown with dashed lines. Instead of a single first reactor unit and/or a single second reactor unit illustrated in FIG. 1, a reaction zone comprising more than one reactor unit configured to carry out the reactions can be used.

DETAILED DESCRIPTION

In the following description, like reference signs denote like elements or steps.

The term oxygen containing moderator refers to a compound which contains oxygen, such as an oxygenate or a compound containing oxygen, carbon, and hydrogen.

As used herein, the term "comprising" includes the broader meanings of "including", "containing", and "comprehending", as well as the narrower expressions "consisting of" and "consisting only of".

In an embodiment the process is carried out at an industrial scale, and preferably as a continuous process.

Unless otherwise specified, amounts expressed as % are weight-%, i.e. wt-%. Values referring to recycle ratio may refer to wt-% or to % as such.

In an embodiment the process steps are carried out in the sequence identified in any aspect, embodiment, or claim. In another embodiment any process step specified to be carried out to a product or an intermediate obtained in a preceding process step is carried out directly to said product or intermediate, i.e. without additional, optional or auxiliary processing steps that may chemically and/or physically alter the product or intermediate between said two consecutive steps.

In another embodiment the present process is run as a continuous process, during which at least some of the steps identified in any aspect, embodiment, or claim occur simultaneously when the process is running.

Any process step specified herein may additionally involve analysis of the reactants, reaction products, and/or operating parameters. For example, chemical composition of a reaction mixture in a reactor unit, feed, or stream can be analyzed, and the analysis result can be used to change a process parameter such that a desired outcome is achieved.

In the context of the present invention the term reactor feed refers to any feed which enters a reactor unit. For simplicity, when at least one same component, such as an olefin monomer or isobutene, is fed into the reactor unit via multiple feeds, a reactor feed of olefin monomers, or an olefin monomer reactor feed, may in such cases mean the total feed of said olefin monomers into the reactor unit.

The terms fresh olefin monomer feed and fresh olefin monomer refer to olefin monomers that are fresh, i.e. non-recycled, and that are fed into the reactor unit to provide a source of olefin monomers to supplement the amount of olefin monomers that are consumed in the course of catalytic reactions in the reactor unit, and that are removed from the reactor unit primarily as a recovered or consumed olefin trimer or olefin tetramer product. The fresh olefin monomers are fed into the first reactor unit in an amount which is sufficient to maintain the weight ratio of monomers to dimers at a desired level.

In an embodiment the olefin monomers are fed into the reactor unit predominantly as a fresh olefin feed, i.e. the fresh olefin monomers constitute more than 50 weight-% of the total olefin monomers that enter the reactor unit. In another embodiment at least 55 weight-%, 60 weight-%, 70 weight-%, 80 weight-% or 90 weight-% of the olefin monomers that enter the reactor unit are fresh.

In an embodiment the recycle feed comprises unreacted olefin monomers. The recycle feed may also comprise solvent.

The term reactor unit refers to a reactor such as at least one reactor unit, or at least one reactor vessel, wherein catalytic reactions are carried out. The reactor unit may comprise at least one catalyst bed and openings for conducting fluids into the reactor unit and for removing fluids from the reactor unit.

An olefin is a compound composed of at least hydrogen and carbon, and which has at least one double bond between two carbon atoms. Olefins suitable for the present process contain two or more carbon atoms and they may be linear or branched. A preferable olefin monomer in the present disclosure contains one double bond. A more preferred olefin monomer is isobutene.

An olefin mixture may also be used in the present process and fed into the first reactor unit, such as a mixture of olefin monomers, olefin dimers and heavier polymers, or a mixture containing olefin monomers with varying number of carbon atoms and double bonds. In an embodiment a feed comprising an olefin monomer mixture is fed into the reactor unit as a mixed feed. Preferably such a monomer mixture predominantly contains one olefin monomer.

In the context of the present invention the mixed feed or a mixed monomer feed means olefins having different carbon numbers, or a mixture of olefin isomers having the same carbon number, as well as their combination. In an embodiment the mixed feed comprises C4-C5 olefins, preferably olefins having one double bond. In another embodiment the mixed feed comprises olefins having a carbon number C4+/−1. In an embodiment reactive components that are lighter than C4 olefins are removed from the feed entering the reactor unit to facilitate distillation of the reaction products.

In an embodiment the olefin monomer feed comprises at least one of the following: C4 olefins, C5 olefins, a mixed feed of C4 and C5 olefins, isobutene, 1-butene, cis-2-butene, trans-2-butene; and optionally inerts, n-butane, i-butane, butadiene, distillation fraction, or any mixture thereof.

In another embodiment the olefin monomer feed, or the mixed feed, comprises or essentially consists of isobutene and at least one of C4 olefins, C5 olefins, a mixed feed of C4 and C5 olefins, 1-butene, cis-2-butene, trans-2-butene, inerts, n-butane, i-butane, butadiene, distillation fraction, or any mixture thereof. In a preferable embodiment isobutene is the major component of the mixed feed.

In an embodiment the olefin monomer contains one double bond.

In an embodiment the olefin monomer is isobutene. Isobutene is a preferred olefin monomer because it can react sequentially with itself and form longer olefinic products such as olefin dimers, olefin trimers and olefin tetramers.

In an embodiment the olefin trimer and/or the olefin tetramer synthesized during the process contains one double bond, i.e. they are iso-olefins. In a preferred embodiment the olefin trimer is a trimer of isobutene and/or the olefin tetramer is a tetramer of isobutene.

In an embodiment the amount of non-reactive components such as inerts, n-butane, and i-butane in the reactor outlet streams that exits the reactor unit(s), is so low that they do not significantly hamper separation of olefin dimers and olefin trimers in the distillation step.

The first reactor outlet stream, which is withdrawn from the first reactor unit, contains at least olefin monomers and olefin dimers, and optionally smaller amounts of moderator and/or inerts.

In an embodiment fresh monomers are fed into the reactor as a high purity monomer feed. High purity olefins have preferably a purity of at least 95 weight-%. High purity olefins have an advantage of allowing more control over the process, in particular the distillation steps and the composition of the end product.

In the context of the present invention the term diluent means any inert agent, or an agent which is less reactive than olefins in the present process. Addition of diluent into the reactor thus lowers the concentration of the olefins in the reactor unit(s), and the rate of the catalytic conversion of olefin monomers, olefin dimers and olefin trimers in the process can be controlled by selecting an appropriate amount of diluent.

Instead of using a single reactor unit as the first reactor unit and/or the second reactor unit, each reactor unit can be sized and distributed into separate vessels, thereby forming a first and/or second reaction zone, correspondingly. By increasing the number of reactor vessels and reactor beds, the reaction conditions are easier to control, and consequently an almost complete olefin monomer, such as isobutene, once-through conversion can be achieved. Thermal control of adiabatic temperature rise is also easier when a plurality of reactor vessels is used.

In an embodiment the reactor unit is comprised of a plurality of reaction vessels arranged as a serial reactor unit or a parallel reactor unit, or their combination.

In an embodiment the reactor unit, such as a first reactor unit or a second reactor unit, is a reaction zone which may comprise one or more reactor vessels.

In an embodiment the reactor unit(s) comprises more than one reactor vessel, such as two, three, four or five reactor vessels each having at least one reactor bed. Use of more than one reactor vessel is advantageous because it allows more detailed control of the temperature, and further allows controlling the amount of moderator and catalyst in each separate reactor vessel. Between the reactor vessels the temperature of the feed can be controlled by temperature control units that are configured to cool or heat the feed. In an embodiment the reaction conditions such as temperature and pressure are essentially the same in each reactor vessel.

When multiple reactor vessels are used as a reactor unit instead of a single reactor vessel, each of the reactor vessels contains a catalyst, preferably an acidic ion exchange resin catalyst. Preferably the same catalyst is used in each reactor vessel. Preferably the amount of catalyst is kept low in the first reactor vessel, and the amount is increased in the subsequent reactor vessels in the downstream direction of the process. By limiting the amount of catalyst in the first reactor vessel(s) e.g. the temperature is easier to control, and the reaction conditions can be maintained in the selected ranges more easily. For example olefins are easier to be kept in liquid phase when a plurality of reactor vessels are used and the olefin stream is cooled between the reactor vessels. Preferably, in addition to the reactor feed into the first reactor vessel, no further olefins are fed into subsequent reactor vessels during the process, i.e. the fed mixture of olefins is not supplemented with further olefins as the mixture flows through the reactor vessels. When a plurality of reactor vessels is used with a single reactor bed in each reactor vessel, the amount of catalyst may increase in the reactor vessels. In a multiple reactor configuration the upstream reactor vessels contain more catalyst than downstream reactor vessels. In an embodiment a multiple reactor unit configuration comprises 3 or 4 reactor vessels.

In a reactor unit containing a plurality of reactor vessels, the volume of the reactor vessels may increase from the first reactor vessel to the subsequent reactor vessel(s) in the downstream direction. In an embodiment the volume of the first and the second reactor vessels is substantially the same. In another embodiment the volume of the third and fourth reactor vessels is substantially the same. In yet another embodiment the volume of the third and fourth reactor vessels is substantially identical with respect to each other, but their volume is larger than the volume of the first or second reactor vessels, where the first and the second reactor vessels may have substantially identical volume.

In an embodiment the oxygen-containing moderator, or moderator, is an oxygenate, such as demiwater (demineralized water) or tert-butylalcohol (TBA). Alternatively or additionally, the moderator comprises an alcohol formed inside the reactor unit as a result of a reaction between water and an olefin. Consequently, e.g. 2-butanol may form from isobutene inside the reactor unit and serve as a moderator.

The moderator may circulate in the recycle loop together with lighter components and is supplemented to keep its amount at a substantially constant level. The amount of moderator can be determined e.g. from a recycle line by known methods. The moderator is preferably used in an amount which exceeds the amount of possible water present in the fresh olefin feed or in the recycle feed, which could also serve as a source of oxygenates, but which alone is not sufficient in the present invention. The moderator can be fed into the reactor unit by mixing it with a feed entering the first reactor unit or the second reactor unit, such as a reactor feed comprising fresh olefin monomers. Alternatively, the moderator can be mixed into any recycle stream before mixing with the fresh or recycled olefin monomers. Use of added moderator in the present process is advantageous because it improves selectivity for trimer production.

In case the monomer olefin is isobutene, resulting oligomers are highly branched pentamethylheptenes and heptamethylnonenes. The product may be optionally hydrogenated in order to achieve corresponding paraffinic products, which have interesting properties as aviation fuel components or chemicals.

In an embodiment the present process is a continuous process. Advantageously the present process allows running the process for a long time, even months, without a need to interrupt the process for maintenance.

In an embodiment the catalytic reactions are carried out at operational conditions wherein the olefins remain in liquid phase, an optionally wherein the moderator remains in liquid phase. Preferably at least the temperature and the pressure of the reactor unit(s) are selected such that the olefins are in liquid phase in the reactor unit.

In one embodiment the first reactor unit and in the second reactor unit are operated in conditions wherein the olefins remain in the same phase, preferably in liquid phase.

In an embodiment the catalyst is a solid catalyst.

In an embodiment the dimerization catalyst is an acid catalyst, preferably a strongly acidic ion exchange resin catalyst, most preferably macroreticular acid ion exchange resin catalyst.

In an embodiment the second catalyst is not the same catalyst as the first catalyst. However, preferably both catalysts are similar types of catalysts, such as acid catalysts.

In an embodiment olefin dimers are fed both to the first reactor unit and to the second reactor unit. This operation mode produces both olefin trimers and olefin tetramers that can be withdrawn in the second reactor outlet stream. Additional controlling of the composition of the second reactor outlet stream can be made by controlling the amount of olefin dimers from the second distillate that is recycled to the first reactor unit and to the second reactor unit. By increasing the amount of recycled dimers in the first reactor unit a reaction between olefin dimer and olefin monomer is favoured thereby producing olefin trimers, whereas by increasing the amount of olefin dimers in the second reactor unit a reaction between olefin dimers is favoured thereby producing olefin tetramers.

In an embodiment the process further comprises recovering heat from at least one stream obtained from a distillation column.

In an embodiment of the process, the recovered heat is used to heat any reactor outlet stream before it enters a distillation column. In another embodiment the heat is used to heat the reactor feed before it enters the reactor unit.

In an embodiment the first distillation column and the second distillation column are non-reactive distillation columns. A non-reactive distillation column in this context is a distillation column which does not contain catalytic material or a reactive zone, and in which the olefins do not significantly react chemically either with each other, or with other chemical agents. The non-reactive distillation column is thus differentiated e.g. from reactive distillation columns that have a reactive zone or a catalytic zone which chemically converts feed components, in particular olefin monomers or olefin dimers or olefin trimers.

In an embodiment each distillation column is operated in conditions where dimerization or oligomerization of the olefins does not occur.

In an embodiment the amount of olefin monomers is analyzed in the first distillate, and/or the first bottom product. The amount of fresh olefin monomers fed into the first reactor unit can thus be adjusted based on the amount of recycled olefin monomers in order to keep the total amount of fed olefin monomers in a desired amount. Similarly, the reactions in the second reactor unit are easier to control when the amount of dimers in the first bottom product is known.

In an embodiment the amount of olefin dimers is analyzed in the second distillate. When the dimer content of the second distillate is known, the controlling of the olefin trimer and/or olefin tetramer production is easier to control. For example, the feed ratio of the recycled olefin dimers from the second distillate to the feed from the first bottom product can be adjusted such that the second reactor unit receives the desired amount of olefin dimers. This embodiment is particularly useful when olefin tetramers are produced, or when the amount of olefin tetramers compared to olefin trimers is increased.

Similarly, the known amount of olefin dimers, and olefin tetramers, in the second distillate can be used to select an appropriate amount of recycled olefin dimers fed into the first reactor unit. This is particularly useful when olefin trimers, or olefin tetramers, are produced in desired amounts.

In an embodiment the catalytic reactions are carried out in liquid phase, preferably fully in liquid phase.

In an embodiment the second reactor outlet stream contains at least 15 weight-% olefin tetramers, such as tetramers of isobutene.

The olefin conversion system 100 is further described by a reference to FIG. 1, wherein
- 110 is a reservoir for olefin monomers;
- 111 is a first reactor feed line;
- 210 is a first reactor unit;
- 211 is a first reactor outlet stream line;
- 310 is a first distillation column;
- 315 is a first recycle line;
- 333 is an optional solvent make-up line
- 350 is a first bottom product line;
- 410 is a second reactor unit;
- 411 is a second reactor outlet stream line;
- 510 is a second distillation column;
- 515 is second recycle line;
- 5151 is a part of the second recycle line connecting the second distillation column to the first reactor unit;
- 5152 is a part of the second recycle line connecting the second distillation column to the second reactor unit;
- 550 is a second bottom product line;
- 590 is a reservoir for an end product;
- 610 is an optional third distillation column;
- 690 is a reservoir for another end product in case where the system comprises the optional third distillation column, this reservoir may receive olefin tetramers from the third distillation column;
- 695 is a reservoir for another end product in case where the system comprises the optional third distillation column, this reservoir may receive olefin trimers from the third distillation column; and
- 555 is an optional third column feed line.

In an embodiment the olefin conversion system further comprises means configured to allow feeding olefin dimers into at least one of the first reactor unit(s); and/or to allow feeding olefin dimers into at least one of the second reactor unit(s). In an embodiment said means include control means that control operation of the olefin conversion system and in particular its feeds, reactors, distillation columns and lines used to transfer feed. The control means can thus be used to direct feeds between different parts of the system. Said means can in particular be used to control the recycling of dimers from the second distillation column to the first reactor unit, and from the second distillation column to the second reactor unit in order to control the production of olefin trimers and olefin tetramers in the system.

Implementation and embodiments are further disclosed in the following numbered clauses:

Clause 1: A process for controlled manufacturing of olefin trimers and olefin tetramers comprising:
a. feeding at least one olefin monomer and at least one oxygen-containing moderator into at least one first reactor unit containing a catalyst;
b. operating at least one of the first reactor unit(s) at a temperature selected from the range 30-140° C. and at a pressure selected from the range 800-5000 kPa for carrying out catalytic reactions between olefins inside the first reactor unit;
c. withdrawing a first reactor outlet stream from at least one of the first reactor unit(s);
d. distilling the first reactor outlet stream in a first distillation column to separate at least a first distillate comprising at least unreacted olefin monomers, and a first bottom product comprising at least dimers of the olefin monomers;
e. feeding the first bottom product into at least one second reactor unit containing a catalyst;
f. operating at least one of the second reactor unit(s) at a temperature selected from the range 30-140° C. and at a pressure selected from the range 150-5000 kPa for carrying out catalytic reactions between olefins inside the second reactor unit;
g. withdrawing a second reactor outlet stream from at least one of the second reactor unit(s); and
h. distilling the second reactor outlet stream in a second distillation column to separate a second distillate comprising at least olefin dimers, and a second bottom product comprising at least trimers and/or tetramers of the olefin monomers; and wherein
the process further comprises controlling the composition of the second reactor outlet stream by:
feeding olefin dimers into at least one of the first reactor unit(s) to increase the amount of olefin trimers in the second reactor outlet stream; and/or
feeding olefin dimers into at least one of the second reactor unit(s) to increase the amount of olefin tetramers in the second reactor outlet stream.

Clause 2: The process of clause 1, wherein at least a portion of the olefin dimers formed during the process are recycled to at least one of the first reactor unit(s) and/or to at least one of the second reactor unit(s), and wherein a recycling ratio of the olefin dimers between the first reactor unit and the second reactor unit is selected from the range 0-100%.

Clause 3: The process of clause 1 or 2, wherein the operating temperature of at least one of the first reactor unit(s) and/or at least one of the second reactor unit(s) is selected from the range 40-120° C. or from the range 45-110° C.

Clause 4: The process of any one of clauses 1-3, wherein the operating weight hour space velocity of at least one of the first reactor unit(s) is selected from the range 1-10 1/h, and/or the operating weight hour space velocity of at least one of the second reactor unit(s) is selected from the range 0.05-100 1/h.

Clause 5: The process of any one of clauses 1-4, wherein the operating pressure of at least one of the first reactor unit(s) is selected from the range 2400-3000 kPa, and/or the operating pressure of at least one of the second reactor unit(s) is selected from the range 1900-2300 kPa.

Clause 6: The process of any one of clauses 1-5, wherein the amount of the oxygen-containing moderator in at least one of the first reactor unit(s) is selected from the range 1000-15000 mol-ppm and/or the amount of the oxygen-containing moderator in at least one of the second reactor unit(s) is selected from the range 10-10000 mol-ppm or 10-2500 mol-ppm.

Clause 7: The process of any one of clauses 1-6, wherein the solvent feed fraction is 0-80 weight-%, preferably 0-60 weight-%.

Clause 8: The process of any one of clauses 1-7, wherein the inert solvent to fresh olefin monomer is selected from the range 0-80 weight-%.

Clause 9: The process of any one of clauses 1-8, wherein the olefin monomers comprise olefins having four carbon atoms, preferably isobutene.

Clause 10: The process of any one of clauses 1-9, wherein the olefin monomers are fed into at least one of the first reactor unit(s) in an olefin feed comprising at least one of the following: C4 olefins, C5 olefins, a mixed feed of C4 and C5 olefins, isobutene, 1-butene, cis-2-butene, trans-2-butene or any mixture thereof; and optionally comprising inerts, n-butane, i-butane, butadiene, distillation fraction, or any mixture thereof.

Clause 11: The process of any one of clauses 1-10, wherein the catalyst is an acid catalyst, preferably a strongly acidic ion exchange resin catalyst, most preferably macroreticular acid ion exchange resin catalyst.

Clause 12: The process of any one of clauses 1-11, wherein the oxygen-containing moderator comprises water, demiwater, alcohol, tert-butyl alcohol, or any combination thereof.

Clause 13: The process of any one of clauses 1-12, comprising increasing the amount of olefin trimers in the final product stream by recycling olefin dimers present in the second distillate to at least one of the first reactor unit(s).

Clause 14: The process of clause 13, wherein 0-50 weight-% of the olefin dimers present in the second distillate are recycled to at least one of the first reactor unit(s) to obtain a ratio of trimers to tetramers of 25-0.05 (wt/wt) in the second reactor outlet stream.

Clause 15: The process of any one of clauses 13-14, comprising distilling the second bottom product in a third distillation column to separate a third distillate comprising trimers of the olefin monomers, and a third bottom product comprising tetramers of the olefin monomers.

Clause 16: The process of any one of clauses 1-15 comprising increasing the amount of olefin tetramers in the second reactor outlet stream by recycling olefin monomers of the first distillate to at least one of the first reactor unit(s) in order to increase the production of olefin dimers in the first reactor unit, by feeding the first bottom product to at least one of the second reactor unit(s), and by recycling olefin dimers of the second distillate to at least one of the second reactor unit(s).

Clause 17: The process of clause 16, wherein 99-100 weight-% of the olefin monomers present in the first distillate are recycled into at least one of the first reactor unit(s) and the first bottom product contains 2-98 weight-% of olefin dimers.

Clause 18: The process of any one of clauses 16-17, wherein dimers are recycled only to at least one of the second reactor unit(s).

Cause 19: An olefin conversion system configured to carry out the process of clauses 1-17 and comprising:
at least one first reactor unit configured to receive an acid catalyst;
at least one second reactor unit configured to receive an acid catalyst;
a first distillation column configured to separate olefin monomers from olefin dimers;
a second distillation column configured to separate olefin dimers from olefin trimers and olefin tetramers;

at least one first reactor unit feed line in fluid connection with at least one of the first reactor unit(s), and at least one reservoir for olefin monomers;

a first reactor unit outlet stream line in fluid connection with at least one of the first reactor unit(s) and the first distillation column;

a first recycle line in fluid connection with at least one of the first reactor unit(s) and the first distillation column;

a first bottom product line in fluid connection with the first distillation column and at least one of the second reactor unit(s);

a second reactor outlet stream line in fluid connection with at least one of the second reactor unit(s) and the second distillation column;

a second recycle line in fluid connection with the second distillation column, at least one of the first reactor unit(s), and at least one of the second reactor unit(s);

a second bottom product line in fluid connection with the second distillation column and a reservoir for the end product; and an optional third distillation column configured to separate olefin trimers from olefin tetramers and comprising a third column feed line in fluid connection with the second bottom product line; and an optional solvent make-up line connected to the first reactor feed line.

Examples

The following examples are provided to better illustrate the claimed invention and they are not to be interpreted as limiting the scope of the invention, which is determined by the claims. To the extent that specific materials are mentioned, they are mentioned merely for illustrating the invention without any limitation thereto. One skilled in the art may develop equivalent means or reactants without exercising inventive capacity and without departing from the scope of the invention.

Table 1 demonstrates some operation modes of the present process. In these examples the present process and olefin conversion system were used. The process equipment was the same in all three examples. The feed was pure isobutene, which serves in this example as an example of an olefin monomer which can be converted to an olefin dimer, an olefin trimer and/or an olefin tetramer by the present process. Changes in the end product composition were achieved by adjusting the process parameters as indicated in Table 1. As can be seen from the results, the whole product range from maximal trimer to maximal tetramer with higher than 99% yield could be produced with the process according to this invention. In the examples a reaction zone corresponds to the term at least one reactor unit used elsewhere in this application.

In Example 1 the target was to maximize trimer yield. In order to minimize the tetramer production, dimers from the second reactor zone were not allowed to enter the second reaction zone. In this case the recycle stream from the first distillation column to the first reaction zone consisted of dimers, unreacted monomers and oxygenate. Oxygenate was kept at a low level (~0.3 mol-%) at the first reaction zone. Solvent addition was omitted because the large recycle stream was a sufficient diluent in itself. Recycle rate from the first distillation column to the first reaction zone per fresh feed rate was 3.4. In this case no recycle from the second distillation column to the first reaction zone was necessary.

In Example 2 the target was to produce about an equal amount of both olefin trimers and olefin tetramers. In this case a sufficient level of dimers were maintained at both the first and the second reaction zones. Consequently, the recycle stream from the first distillation column to the first reaction zone contained dimers, monomers and oxygenate. The oxygenate content entering the first reaction zone was kept at intermediate level (~1%). The recycle stream from the second distillation column to the first reaction zone and to the second reaction zone consisted of dimers and oxygenate. Recycle rate from the first distillation column to first reaction zone per fresh feed rate was 3.2. Recycle rate from the second distillation column to the second reaction zone per fresh feed rate was 1.0. The additional solvent was unnecessary because the recycle streams provided sufficient dilution. In this mode maintaining sufficient dimer content in the feed to the first reaction zone, as well as to the second reaction zone, required application of a recycle from the second distillation column to the first reaction zone. Recycle rate from the second distillation column to the first reaction zone per fresh feed rate was 0.2.

In Example 3 the target was to maximize tetramer production. In this case trimer production in the primary reaction zone was minimized and therefore dimer was not recycled to the primary reaction zone, but this recycle stream to the first reaction zone consisted of solvent, monomers and oxygenate. Oxygenate content was relatively high to suppress trimer formation (~1.5%). In this case it was necessary to provide additional diluent to the feed to the first reaction zone. The solvent retarded the reactions and absorbed the heat of reaction so that the process remained controllable. The recycle stream from the second distillation column to the second reaction zone consisted mainly of dimers and a small amount of oxygenate. Recycle rate from the first distillation column to the first reaction zone per fresh feed rate was 3.07. Recycle from the second distillation column to the first reaction zone was not useful in this mode and consequently the rate of this stream was 0. Recycle rate from the second distillation column to second reaction zone per fresh feed rate was 1.4.

TABLE 1

Exemplary operation modes of the present process.

| Run Mode | | Example 1 maximum trimer | Example 2 trimer/ tetramer, about 1:1 | Example 3 maximum tetramer |
|---|---|---|---|---|
| WHSV | | | | |
| First reaction zone | 1/h | 1.11 | 1.11 | 1.03 |
| Second reaction zone | 1/h | 0.15 | 0.34 | 0.36 |
| Temperature | | | | |
| First reaction zone | ° C. | 100 | 100 | 88 |
| Second reaction zone | ° C. | 40 | 100 | 100 |
| Pressure | | | | |
| First reaction zone | kPa | 2600 | 2600 | 2600 |
| Second reaction zone | kPa | 2100 | 2100 | 2100 |
| Oxygenate level | | | | |
| First reaction zone | mol-% | 0.3 | 1.0 | 1.5 |
| Second reaction zone | mol-% | 0 | 0.15 | 0.125 |
| Solvent content | | | | |
| First reaction zone | mol-% | 0 | 0 | 71 |
| Second reaction zone | mol-% | 0 | 0 | 0 |
| Recycle rates*) | | | | |
| From 1st distillation column to 1st | | 3.4 | 3.2 | 3.07 |

TABLE 1-continued

Exemplary operation modes of the present process.

| Run Mode | Example 1 maximum trimer | Example 2 trimer/ tetramer, about 1:1 | Example 3 maximum tetramer |
|---|---|---|---|
| reaction zone | | | |
| From 2nd distillation column to 2nd reaction zone | 0.0 | 1.0 | 1.4 |
| From 2nd distillation column to 1st reaction zone | 0.0 | 0.2 | 0.0 |
| Oligomer yield | | | |
| all oligomers | 99.8 wt-% | 99.8 wt-% | 99.0 wt-% |
| trimer | 96.0 wt-% | 50.0 wt-% | 4.8 wt-% |
| tetramer | 3.8 wt-% | 49.8 wt-% | 93.9 wt-% |
| Weight ratio trimer/tetramer in final product | 25.20 | 1.00 | 0.05 |

*)The flow rates are scaled by dividing the total weight flow rate by the flow rate of the fresh olefin feed.

The foregoing description has provided by way of non-limiting examples of particular implementations and embodiments a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, it shall be understood that many variations can be made in the procedures described herein while still remaining within the scope of the present invention. Additionally, any individual feature of any embodiment may be used without the presence of the other features of the embodiment.

The invention claimed is:

1. A process for controlled manufacturing of olefin trimers and olefin tetramers comprising:
   a. feeding at least one olefin monomer and at least one oxygen-containing moderator into a first reactor unit containing a catalyst, wherein the at least one oxygen-containing moderator is a compound which contains oxygen, is an oxygenate, or is a compound including oxygen, carbon, and hydrogen;
   b. operating the first reactor unit at a temperature selected from a range of 30-140° C. and at a pressure selected from a range of 800-5000 kPa for carrying out catalytic reactions between olefins inside the first reactor unit;
   c. withdrawing a first reactor outlet stream from the first reactor unit;
   d. distilling the first reactor outlet stream in a first distillation column to separate at least a first distillate including at least unreacted olefin monomers, and a first bottom product including at least dimers of the olefin monomers;
   e. feeding the first bottom product into a second reactor unit containing a catalyst;
   f. operating the second reactor unit at a temperature selected from a range of 30-140° C. and at a pressure selected from a range of 150-5000 kPa for carrying out catalytic reactions between olefins inside the second reactor unit;
   g. withdrawing a second reactor outlet stream from the second reactor unit; and
   h. distilling the second reactor outlet stream in a second distillation column to separate a second distillate including at least olefin dimers, and a second bottom product including at least trimers and/or tetramers of the olefin monomers; and wherein:

the process comprises:
      controlling a composition of the second reactor outlet stream by:
         i. feeding the olefin dimers of the second distillate and/or olefin dimers from an external source into the first reactor unit to increase an amount of olefin trimers in the second reactor outlet stream; and/or
         ii. feeding the olefin dimers of the second distillate and/or olefin dimers from the external source into the second reactor unit to increase an amount of olefin tetramers in the second reactor outlet stream.

2. The process of claim 1, comprising:
   recycling at least a portion of the olefin dimers of the second distillate formed during the process to the first reactor unit and/or the second reactor unit, and wherein a recycling ratio of the olefin dimers of the second distillate between the first reactor unit and the second reactor unit is selected from a range of 0-100%.

3. The process of claim 1, wherein the operating temperature of the first reactor unit and/or the second reactor unit is selected from a range of 40-120° C. and/or from a range of 45-110° C.

4. The process of claim 1, wherein an operating weight hour space velocity of the first reactor unit is selected from a range of 1-10 1/h, and/or an operating weight hour space velocity of the second reactor unit is selected from a range of 0.05-100 1/h.

5. The process of claim 1, wherein the operating pressure of the first reactor unit is selected from a range of 2400-3000 kPa, and/or the operating pressure of the second reactor unit is selected from a range of 1900-2300 kPa.

6. The process of claim 1, wherein an amount of the oxygen-containing moderator in the first reactor unit is selected from a range of 1000-15000 mol-ppm and/or an amount of the oxygen-containing moderator in the second reactor unit is selected from a range of 10-10000 mol-ppm or 10-2500 mol-ppm.

7. The process of claim 1, wherein a solvent feed fraction is 0-80 weight-%, and/or 0-60 weight-%.

8. The process of claim 1, wherein an inert solvent to fresh olefin monomer is selected from a range of 0-80 weight-%.

9. The process of claim 1, wherein the olefin monomers comprise:
   olefins having four carbon atoms, and/or isobutene.

10. The process of claim 1, comprising:
    feeding the olefin monomers into the first reactor unit in an olefin feed including at least one or more of the following: C4 olefins, C5 olefins, a mixed feed of C4 and C5 olefins, isobutene, 1-butene, cis-2-butene, trans-2-butene or any mixture thereof; and/or including inerts, n-butane, i-butane, butadiene, distillation fraction, or any mixture thereof.

11. The process of claim 1, wherein the catalyst is an acid catalyst, and/or an acidic ion exchange resin catalyst, and/or macroreticular acid ion exchange resin catalyst.

12. The process of claim 1, wherein the at least one oxygen-containing moderator comprises:
    water, demiwater, alcohol, tert-butyl alcohol, or any combination thereof.

13. The process of claim 1, comprising:
increasing an amount of olefin trimers in a final product stream by recycling the olefin dimers present in the second distillate to the first reactor unit.

14. The process of claim 13, comprising:
recycling 0-50 weight-% of the olefin dimers present in the second distillate to at least the first reactor unit to obtain a ratio of trimers to tetramers of 25-0.05 (wt/wt) in the second reactor outlet stream.

15. The process of claim 13, comprising:
distilling the second bottom product in a third distillation column to separate a third distillate including trimers of the olefin monomers, and a third bottom product including tetramers of the olefin monomers.

16. The process of any one of claim 1 comprising:
increasing an amount of olefin tetramers in the second reactor outlet stream by recycling the olefin monomers present in the first distillate to the first reactor unit in order to increase a production of olefin dimers in the first reactor unit, by feeding the first bottom product to the second reactor unit, and by recycling the olefin dimers present in the second distillate to the second reactor unit.

17. The process of claim 16, comprising:
recycling 99-100 weight-% of the olefin monomers present in the first distillate into the first reactor unit, wherein the first bottom product contains 2-98 weight-% of olefin dimers.

18. The process of claim 16, wherein the olefin dimers of the second distillate are recycled only to the second reactor unit.

19. An olefin conversion system configured for controlled manufacturing of olefin trimers and olefin tetramers, the olefin conversion system comprising:
a. a first reactor unit configured to receive an acid catalyst;
b. a second reactor unit configured to receive an acid catalyst;
c. a first distillation column configured to separate olefin monomers from olefin dimers;
d. a second distillation column configured to separate olefin dimers from olefin trimers and olefin tetramers;
e. at least one first reactor unit feed line in fluid connection with the first reactor unit and at least one reservoir for olefin monomers;
f. a first reactor unit outlet stream line in fluid connection with the first reactor unit and the first distillation column;
g. a first recycle line in fluid connection with the first reactor unit and the first distillation column;
h. a first bottom product line in fluid connection with the first distillation column and the second reactor unit;
i. a second reactor outlet stream line in fluid connection with the second reactor unit and the second distillation column;
j. a second recycle line in fluid connection with the second distillation column, the first reaction unit, and the second reaction unit;
k. a second bottom product line in fluid connection with the second distillation column and a reservoir for an end product;
l. an optional third distillation column configured to separate olefin trimers from olefin tetramers and including a third column feed line in fluid connection with the second bottom product line; and
m. an optional solvent make-up line connected to the first reactor unit feed line.

20. The process of claim 1, comprising:
hydrogenating to achieve paraffinic products.

21. The process of claim 1, wherein the controlling the composition of the second reactor outlet stream comprises:
feeding the olefin dimers from the external source into the first reactor unit to increase the amount of olefin trimers in the second reactor outlet stream; and/or
feeding the olefin dimers from the external source into the second reactor unit to increase the amount of olefin tetramers in the second reactor outlet stream.

22. The process of claim 1, wherein:
the first reactor unit is comprised of a plurality of reaction vessels arranged as a serial reactor unit, a parallel reactor unit, or a combination thereof; and/or
the second reactor unit is comprised of a plurality of reaction vessels arranged as a serial reactor unit, a parallel reactor unit, or a combination thereof.

* * * * *